United States Patent [19]

Houge et al.

[11] Patent Number: 5,320,613
[45] Date of Patent: Jun. 14, 1994

[54] MEDICAL LUMEN FLUSHING AND GUIDE WIRE LOADING DEVICE AND METHOD

[75] Inventors: Reed A. Houge, St. Michael; Thomas V. Ressemann, St. Cloud; Louis G. Ellis, Minneapolis, all of Minn.

[73] Assignee: SciMed Life Systems, Inc., Maple Grove, Minn.

[21] Appl. No.: 1,081

[22] Filed: Jan. 6, 1993

[51] Int. Cl.⁵ ............................................. A61M 5/00
[52] U.S. Cl. ..................................... 604/283; 604/256
[58] Field of Search ................... 604/283, 167, 256, 28

[56] References Cited

U.S. PATENT DOCUMENTS

| | | | |
|---|---|---|---|
| 3,565,078 | 2/1971 | Vailliancourt | 128/349 |
| 4,668,226 | 5/1987 | Omata et al. | 604/283 |
| 4,673,400 | 6/1987 | Martin | 604/283 |
| 4,693,710 | 9/1987 | McCool | 604/283 |
| 4,716,757 | 1/1988 | McGregor et al. | 72/387 |
| 4,726,369 | 2/1988 | Mar | 128/303 |
| 4,829,999 | 5/1989 | Auth | 128/303 |
| 4,907,332 | 3/1990 | Christain et al. | 29/237 |
| 4,946,445 | 8/1990 | Lynn | 604/283 |
| 4,999,048 | 2/1991 | Metzger | 604/283 |
| 5,041,097 | 8/1991 | Johnson | 604/167 |
| 5,057,093 | 10/1991 | Clegg et al. | 604/283 |
| 5,071,413 | 12/1991 | Utterberg | 604/283 |
| 5,209,740 | 5/1993 | Bryant et al. | 604/283 |

OTHER PUBLICATIONS

Article in *Catheterization and Cardiovascular Diagnosis* 28:93-94 (1993) *Letters to the Editor* "Using a Touhy Borst System for Plushing Thin Catheter Lumens Which Do Not Have a Hub for a Syringe", Vishva Dev, MD.

Primary Examiner—Paul J. Hirsch
Attorney, Agent, or Firm—Kinney & Lange

[57] ABSTRACT

A connector for use in flushing or drawing fluid through an inner lumen of a tubular member has a body with a proximal end, a distal end, and a flushing lumen extending therethrough. The body has a distal portion wherein the flushing lumen increases in size from a first proximal cross-sectional area to a second larger distal cross-sectional area so that an annular surface within the distal portion presses against an end of the tubular member when the end of the tubular member is inserted into the distal end of the body. A temporary fluid seal is created between the body and the tubular member when the tubular member is pressed against the annular surface. In one preferred embodiment, a flange is disposed within the connector, the flange being designed so that a portion of the flange extends into the inner lumen of the tubular member when the tubular member is pressed against the annular surface, thereby providing a path for leading a guide wire into the inner lumen. In another embodiment, a longitudinal groove extends the length of the connector to provide for the lateral removal of the connector from a guide wire.

24 Claims, 5 Drawing Sheets

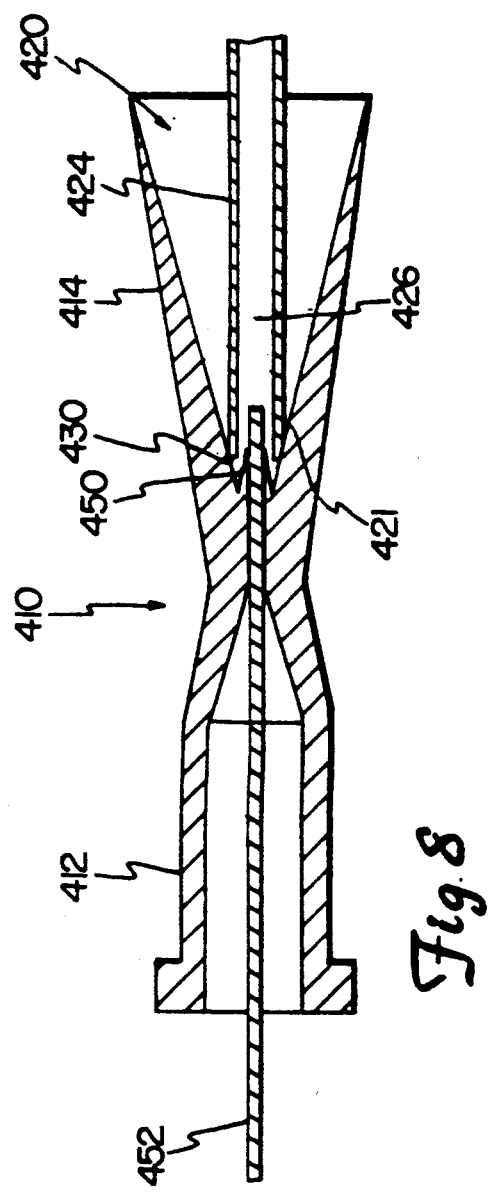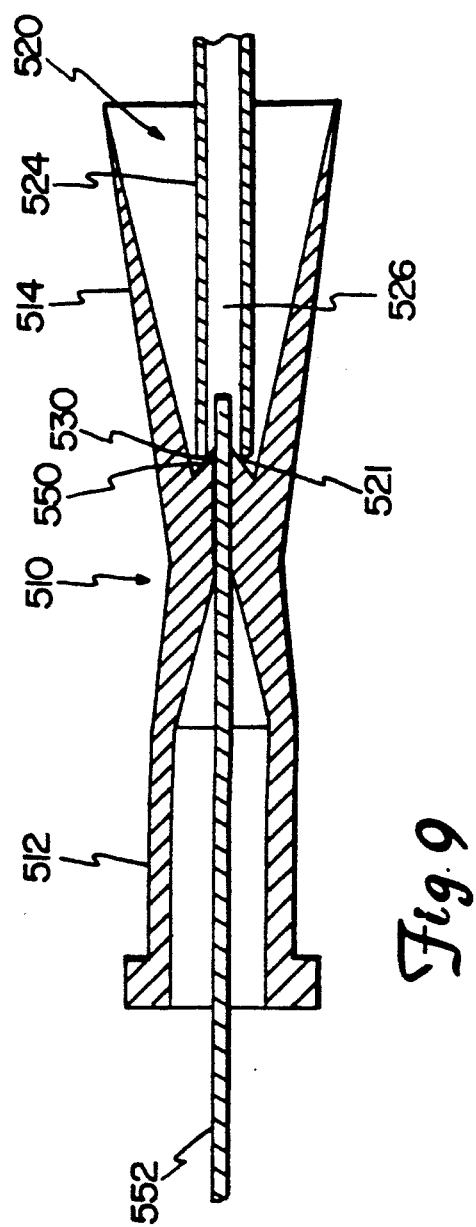

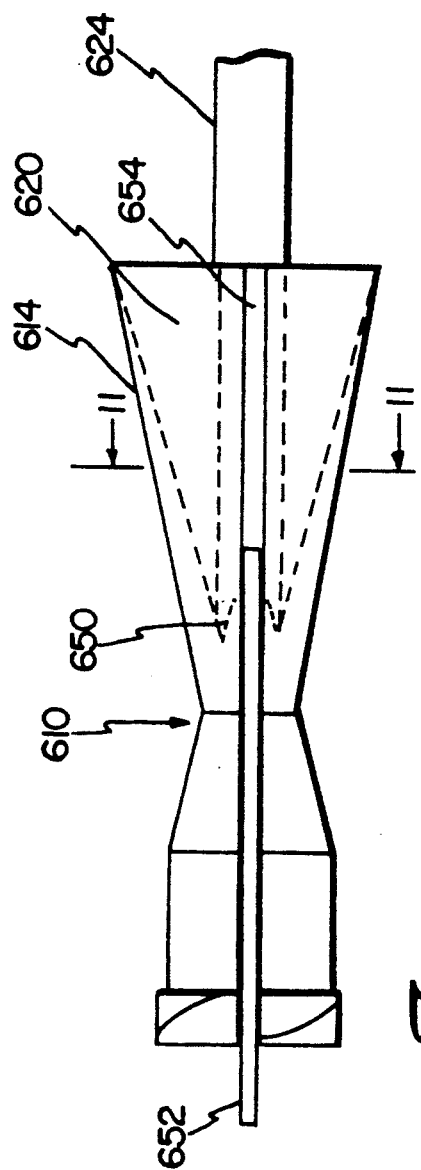
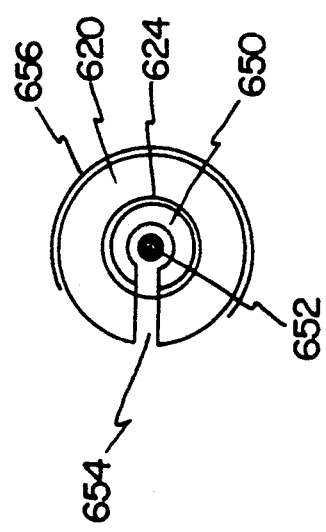

MEDICAL LUMEN FLUSHING AND GUIDE WIRE LOADING DEVICE AND METHOD

BACKGROUND OF THE INVENTION

The present invention relates to the field of medical devices. In particular, the present invention relates to a method and device for removing fluids, tissue and other debris from an inner lumen or chamber of a tubular member of a medical device. In addition, the present invention relates to a method and device for introducing a guide wire into an inner lumen of a tubular member of a medical device.

There are numerous medical procedures that involve inserting tubular members within the body of the patient. In particular, a typical angioplasty procedure requires inserting at least a guide catheter and a dilatation catheter into the vascular system of a patient to open a stenosis within that vascular system. One type of dilatation catheter is an over-the-wire catheter. The standard over-the-wire catheter has an inner or guide wire lumen that extends from the distal end of the catheter to the proximal end of the catheter. A manifold is attached at the proximal end of the catheter to provide an attachment for fluid communication with the guide wire lumen.

A single operator exchange catheter, or S.O.E. catheter, is a variation of the over-the-wire catheter. The S.O.E. catheter has a guide wire lumen that only extends through a portion of the catheter. The guide wire lumen extends from the distal end of the catheter to a distal porthole on the catheter tube.

The guide wire lumen is provided on a standard over-the-wire catheter and an S.O.E. catheter so that a guide wire can be used to establish a path through the vascular system to the stenosis of the patient. The use of the guide wire enables the catheter to be advanced through the blood vessel relatively quickly, thereby reducing the time required for the procedure. In some angioplasty procedures, it may be desirable to use dilatating catheters having different balloon sizes or configurations. Therefore, it is common for the operator to remove a catheter from the vascular system and set that catheter aside to be reinserted at a later time in the procedure.

One concern that arises when the operator attempts to reinsert the catheter into the vascular system relates to the fact that the inner or guide wire lumen of the catheter was in fluid communication with the vascular system of the patient. Therefore, blood and other tissues from the patient may have collected within the guide wire lumen of the catheter. Such blood and tissue may coagulate and block the guide wire lumen of the catheter when the catheter is removed from the vascular system. The coagulated tissue then makes the catheter inoperable, since it prevents the operator from effectively guiding the catheter over the guide wire. Accordingly, the operator must flush the inner lumen of the catheter after removing it from the patient if the operator wants to reinsert the catheter later during the procedure.

The flushing procedure for a standard over-the-wire catheter is relatively simple because a luer-fitting is attached to the manifold on the proximal end of the guide wire lumen. The operator can simply attach a standard syringe to the proximal end of the guide wire lumen and force flushing fluid through the lumen. The flushing procedure for an S.O.E. catheter is more difficult to perform because there is no fitting on either end of the guide wire lumen to connect a syringe to the guide wire lumen.

The standard technique for flushing the inner lumen of an S.O.E. catheter involves inserting a blunt needle into the guide wire lumen of the catheter to provide a means for fluid communication between the guide wire lumen and a syringe connected to the blunt needle. This procedure is inherently difficult to perform and is potentially dangerous. The guide wire lumen of an angioplasty catheter is generally very small in size. For example, an angioplasty dilatation catheter having a guide wire lumen with a diameter as small as 0.016 inches is common in the medical industry. Therefore, it is very difficult to insert a lumen flushing needle (which commonly has an outside diameter of 0.012 inches) within the guide wire lumen of such a catheter. This problem is magnified by the fact that an angioplasty procedure is generally performed in a darkened room, making it very difficult to see the guide wire lumen of the catheter and the needle.

This procedure also creates a situation that is inherently dangerous to the operator. It is extremely easy for the operator to accidently stick a finger while attempting to insert the needle into the lumen ("needle stick"). Such an accident exposes the operator to a potential inadvertent transfer of dangerous or fatal diseases.

There are also numerous medical procedures besides angioplasty that require an operator to use a lumen flushing technique similar to that described above. For example, some tissue collection procedures present the need for removing tissues from a collection chamber to perform further pathological studies on the tissue. It would be advantageous to provide an efficient and effective means to flush the inner lumen of certain medical devices without exposing the operator to the inherent dangers of the current needle-based method.

Another concern that arises during an angioplasty procedure occurs when the operator attempts to load the guide wire into the catheter while the guide wire is in the vascular system of the patient. Generally, the relative diameters of the guide wire and the guide wire lumen make it difficult for the operator to load the guide wire into the inner or guide wire lumen. Once again, this problem is magnified by the fact that the angioplasty procedure is generally performed in a darkened room. This basic problem of loading a guide wire into the guide wire lumen increases the time it takes to exchange a catheter, thereby increasing the time of the procedure. Therefore, it would be advantageous to provide an efficient and quick means to load the guide wire into the guide wire lumen of an angioplasty catheter.

SUMMARY OF THE INVENTION

The present invention is a method and connector for use in flushing an inner lumen of a tubular member. In addition, the present invention relates to a method and connector for introducing a guide wire into an inner lumen of a tubular member of a medical device. The connector has a body with a proximal end and a distal end and a flushing lumen extending therethrough. The body has a distal portion wherein the flushing lumen increases in size from a first proximal cross-sectional area to a second larger distal cross-sectional area. An annular surface within the distal portion of the body presses against an end of the tubular member when the end of the tubular member is inserted into the distal portion of the body. A temporary fluid seal is created between the body and the tubular member when the tubular member is pressed against the annular surface. Once a temporary seal is established, fluid can be forced through the connector and into a first end of the inner lumen to flush fluid and foreign material out of a second end of the inner lumen. Alternatively, this temporary seal permits a suction method whereby a vacuum may be drawn to pull the foreign material from the inner lumen and into the connector.

In one preferred embodiment a flange is disposed within the distal portion of the body. The flange is designed so that a portion of the flange extends into the inner lumen of the tubular member when the tubular member is pressed against the annular surface. One of the purposes of the flange is to provide a path for a guide wire to facilitate an easier insertion of the guide wire into the inner lumen of the tubular member. In addition, the flange can be designed so that the tubular member presses against the flange when the tubular member is inserted into the distal portion of the connector and thereby create a temporary seal between the tubular member and the connector.

In another preferred embodiment, the connector has a longitudinal groove or slot extending along its entire length and communicating with the flushing lumen along its entire length. The groove is designed to permit the removal of the connector from a guide wire. The groove can be covered by the operator to provide a sufficient seal so the operator may also flush the inner lumen of the tubular member with the connector.

In another preferred embodiment the connector has a fitting, such as a luer fitting, on its proximal end for attaching a flushing fluid source to the connector. The flushing fluid source is typically a syringe containing flushing fluid.

The present invention provides a device and method that is easy for the operator to use and which minimizes certain dangers to the operator. The operator inserts one end of the tubular member into the distal end of the connector. The operator presses the tubular member against the annular surface to create a temporary fluid seal between the connector and the tubular member. The operator can then flush the inner lumen by either forcing a flushing fluid through the connector and into the inner lumen of the tubular member or drawing the foreign material from the inner lumen and into the connector.

The present invention is ideally suited for flushing an inner lumen of a tubular member where the inner lumen has a very small diameter. In addition, the shape of the flushing lumen permits the operator to use the connector upon a number of different sized tubular members.

The present invention also provides a device and method for facilitating the insertion of a guide wire into an inner lumen of a tubular member. The operator inserts one end of the tubular member into the distal end of the connector so that at least a portion of a flange within the tubular member extends into the inner lumen. The operator then inserts the guide wire into the flushing lumen at the proximal end of the connector. The connector is then guided through the flushing lumen of the connector and into the inner lumen of the tubular member. In addition, a lateral groove may be provided on the connector to permit the operator to laterally remove the connector from the guide wire.

BRIEF DESCRIPTION OF THE DRAWINGS

FIG. 8 is a sectional view like FIG. 2 of another alternative embodiment of the present invention.

FIG. 9 is a sectional view like FIG. 2 of another alternative embodiment of the present invention.

FIG. 10 is a side view in elevation of an alternative embodiment of the present invention.

FIG. 11 is a sectional view as taken along line 11—11 of FIG. 10.

While the above-identified drawing features set forth preferred embodiments, other embodiments of the present invention are also contemplated, as noted in the discussion. This disclosure presents illustrative embodiments of the present invention by way of representation and not limitation. It should be understood that numerous other modifications and embodiments can be devised by those skilled in the art which fall within the scope and spirit of the principles of this invention.

DETAILED DESCRIPTION OF THE PREFERRED EMBODIMENTS

Figure 1:
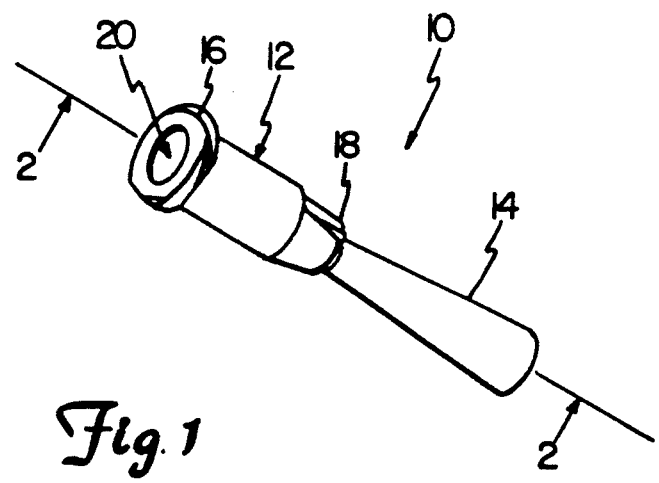
FIG. 1 is a perspective view of a connector incorporating the present invention.
Figure 2:
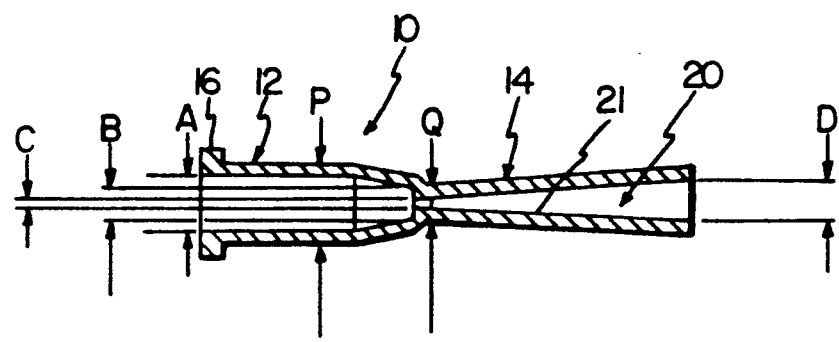
FIG. 2 is a sectional view as taken along line 2—2 of FIG. 1.
Figure 3:
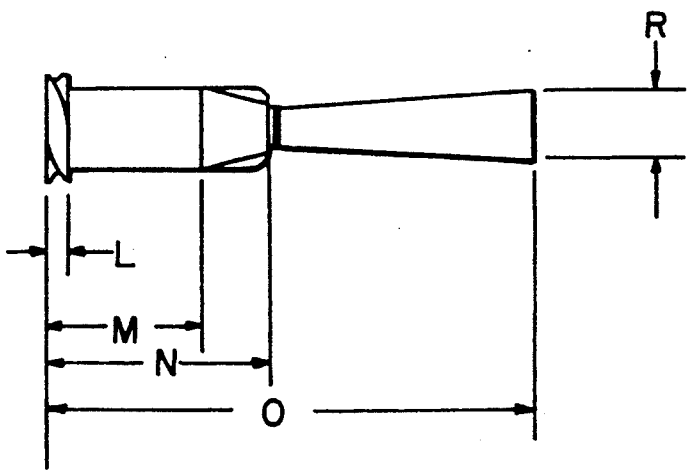
FIG. 3 is a side view in elevation of the present invention.

FIGS. 1-3 show a connector 10 to be used for flushing an inner lumen of a tubular member with fluid from a flushing fluid source. FIG. shows the connector 10 with a generally cylindrical proximal portion 12 and a generally conical distal portion 14. The proximal portion has a luer fitting 16 and wings 18. The wings 18 allow easier manipulation by an operator.

As seen in FIG. 2, the connector 10 has a flushing lumen 20 extending entirely therethrough. In the conical distal portion 14, the flushing lumen 20 defines an interior surface 21 of the connector 10. The flushing lumen has a proximal inside diameter A within the proximal portion 12. The flushing lumen 20 decreases in size as it extends through the proximal portion 12 to an intermediate diameter B, and then to an intermediate diameter C. The flushing lumen 20 then linearly expands within the distal portion 14 to a larger distal inside diameter D.

FIG. 3 shows dimensions L, M, N, and O which define the lengths of various portions of the connector 10. FIG. 3 also shows dimension R which defines the outside diameter of the connector 10 at its distal end. FIG. 2 shows dimensions P and Q which define the outside diameter of the connector at points P and Q.

Figure 4:
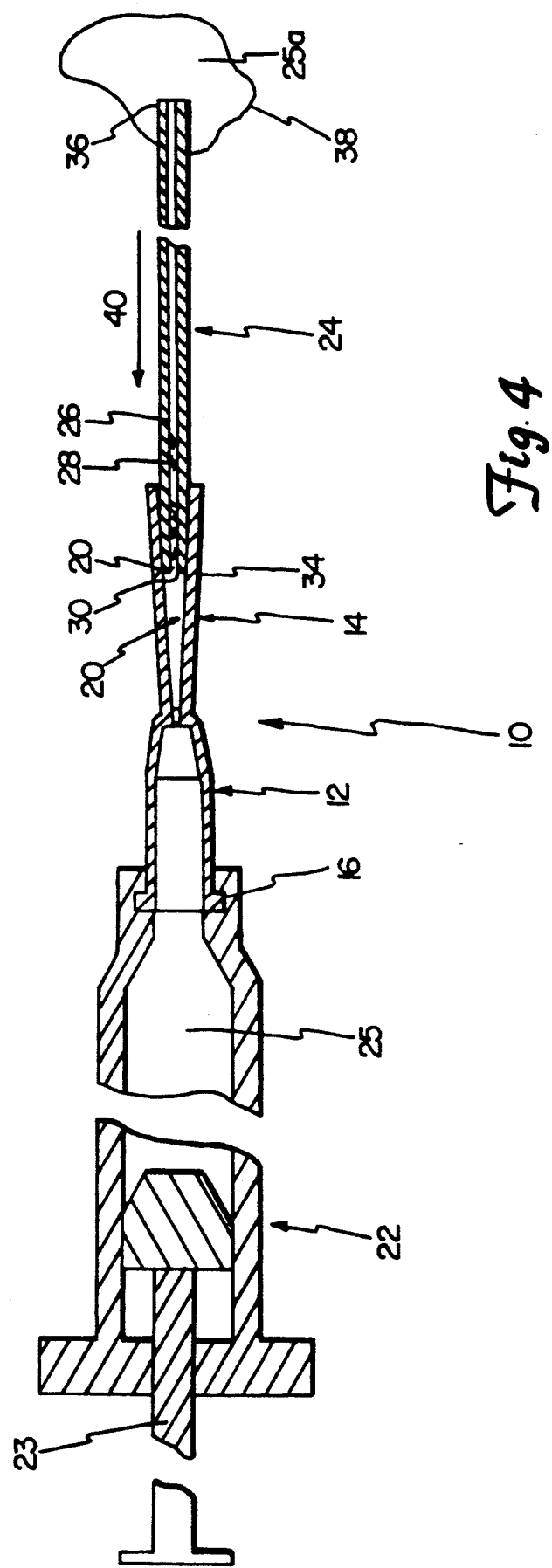
FIG. 4 is a longitudinal sectional view of the present invention connected to a syringe and a tubular member.

FIG. 4 shows the present invention when it is incorporated with a syringe 22 to flush an inner lumen 26 of a tubular member 24. The syringe 22 contains a flushing fluid 25 and is attached to the connector 10. The luer fitting 16 of the connector 10 engages a cooperative fitting on the syringe 22 to provide a fluid-tight seal between the connector 10 and the syringe 22. The syringe 22 has a plunger 23 that provides a means for forcing the flushing fluid 25 out of the syringe and into the connector 10. Alternatively, the plunger 23 also provides a suction means for drawing or pulling fluid from the connector and into the syringe 22.

The tubular member 24 is disposed within the distal portion 14 of the connector 10 as shown in FIG. 4. Body fluids and/or tissue 28 are disposed within an inner lumen 26 of the tubular member 24.

To remove the body fluids 28 from the inner lumen 26 an operator attaches the connector 10 to the syringe 22. The operator further inserts the tubular member 24 within the distal portion 14 of the connector 10. The operator then applies an axially directed force (in the direction of arrow 40 in FIG. 4) to the tubular member 24 so that a first end 30 of the tubular member 24 presses tightly against the interior surface 21 of the connector 10, which is conically shaped and annular in lateral cross-section. The interior surface 21 and/or the first end 30 deform slightly under the pressure of this axial force to form a temporary fluid seal 34 between the connector 10 and the tubular member 24.

The operator then has two alternatives for removing the body fluids 28 from the tubular member 24. The first removal process involves forcing the flushing fluid 25 through the connector 10 and into the first end 30 of the inner lumen 26 by pressing the plunger 23 of the syringe 22. The flushing fluid then forces the body fluids 28 out of a second end 36 of the inner lumen 26.

The second removal process differs from the first in that the operator uses the syringe 22 as a suction source. In one suction method, the operator draws the bodily fluids 28 through the connector 10 and into the syringe 22 by pulling on the plunger 23. This suction method is suitable for S.O.E. catheters. In another suction method, the operator places the second end 36 of the inner lumen 26 in a fluid source 38 containing flushing fluid 25a. The operator then draws the flushing fluid 25a through the inner lumen 26 and the connector 10 and into the syringe 22 by pulling on the plunger 23.

After performing any of the above tubular member flushing methods, the operator can remove the temporary seal 34 by relieving the axial force urging the tubular member 24 and connector 10 together. The tubular member 24 is then removed from the distal portion 14 of the connector 10.

In one preferred embodiment, the dimensions of the connector as diagramed in FIGS. 2 and 3 are as follows: A=0.167 inches, B=0.098 inches, C=0.027 inches, D=0.117 inches, L=0.063 inches, M=0.453 inches, N=0.653 inches, O=1.428 inches P=0.225 inches, Q=0.107 inches and R=0.197 inches.

Figure 5:
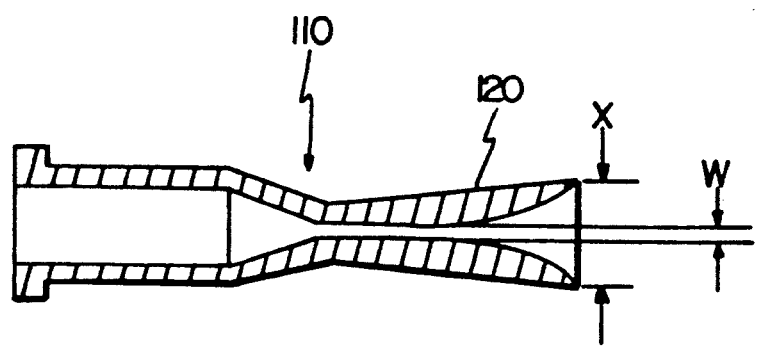
FIG. 5 is a sectional view like FIG. 2 of an alternative embodiment of the present invention.
Figure 6:
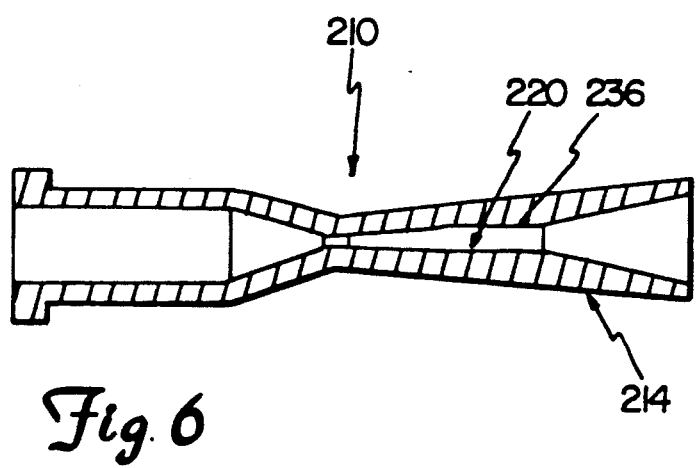
FIG. 6 is a sectional view like FIG. 2 of another alternative embodiment of the present invention.
Figure 7:
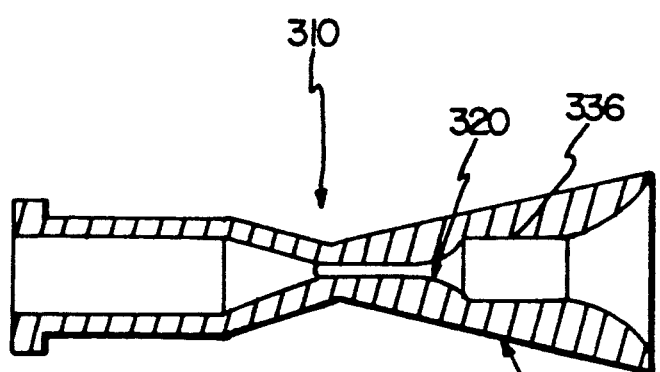
FIG. 7 is a sectional view like FIG. 2 of another alternative embodiment of the present invention.

FIGS. 5, 6 and 7 show the present invention can be formed to provide a temporary fluid seal between the connector and a variety of different shaped medical devices. FIG. 5 shows an alternative connector 110 wherein the flushing lumen 120 within the distal portion of the connector increases nonlinearly in size from a first proximal diameter W to a second, larger distal diameter X. FIG. 6 shows an alternative connector 210 wherein the flushing lumen 220 first increases in size linearly, then stays constant in such a way as to form a "step" 236, then again increases linearly, all within a distal portion 214 of the connector 210. FIG. 7 shows an alternative connector 310 wherein the flushing lumen 320 increases in size nonlinearly, but again has an intermediate constant diameter step 336 within a distal portion 314 of the connector 310. In the three designs shown in FIGS. 5, 6 and 7, the use of the connector for flushing by positive or negative pressurization is the same as described above in connection with the connector of FIGS. 1–4.

In addition to flushing the inner lumen of a tubular member, the connector of the present invention can also be used to load a guide wire into a guide wire lumen on a catheter. However, the devices of FIGS. 1–7 are not ideally designed for loading a guide wire because a distal tip of the guide wire may catch on the first end 30 of the tubular member 34 as the guide wire passes through the distal portion 14 of the connector 10. FIGS. 8 and 9 show preferred alternative embodiments of the present invention which provide a path for the insertion of a guide wire into the inner lumen of the tubular member. FIG. 8 shows a connector 410 with a proximal portion 412, a distal portion 414, and a flushing lumen 420 extending therethrough. A conically-shaped flange 450 is disposed within the distal portion 414 of the connector 410. The flushing lumen 420 within the distal portion 414 of the connector 410 acts as a guide funnel to direct a first end 430 of a tubular member 424 over the flange 450. The flange 450 is designed so that at least a portion of the flange 450 extends into the first end 430 of the tubular member 424 when the first end 430 is pressed against an interior surface 42; of the distal portion of the connector 410. The flange 450 acts like an inner funnel so that once the flange 450 is positioned within the tubular member 430, an operator may insert a guide wire 452 through the connector 410 and into the inner lumen 426 of tubular member 424.

FIG. 9 shows an alternative embodiment wherein a connector 510 has a proximal portion 512, a distal portion 514 and a flushing lumen 520 extending therethrough. A conically-shaped flange 550 is disposed within the distal portion 514 of the connector 510. The flushing lumen 520 within the distal portion 514 acts like a guide funnel to direct a first end 530 of a tubular member 524 over the flange 550. The flange 550 acts like an inner funnel to facilitate the easy insertion of a guide wire 552 into an inner lumen 526 of a tubular member 524. In addition, the connector 510 is designed so a first end 530 of tubular member 524 will press against an interior surface 521 disposed on the flange 550. This particular design is beneficial because it prevents the first end 530 from collapsing as a result of any excessive axial force directed by the operator when attempting to create the temporary seal between the connector 510 and the tubular member 524.

FIGS. 10 and 11 show another preferred embodiment of the present invention. As seen in FIGS. 10 and 11, a longitudinal groove 654 extends throughout the length of the connector 610 and extends through the body of the connector into communication with a flushing lumen 620 in the connector, along the entire length of the flushing lumen. This particular embodiment has a flange 650 disposed within the flushing lumen 620 adjacent a distal portion 614 of the connector. The flange 650 has dimensions similar to those shown in either FIGS. 8 or 9. This embodiment permits the lateral removal of the connector 610 from a guide wire 652 via the longitudinal groove 654. Accordingly, the operator can more easily remove the connector 610 from the guide wire 652 after the guide wire is inserted into a tubular member 624. If the longitudinal groove 654 was not provided, the operator would be required to remove the connector 610 from the guide wire 652 by sliding the connector 610 over the entire length of the guide wire 652. In an S.O.E. catheter exchange procedure where the connector is used as an aid to load an S.O.E. catheter onto the proximal end of a guide wire which is in place within the patient, the connector cannot be slid over the wire for removal. Therefore, lateral removal of the connector from the guide wire is necessary.

The longitudinal groove 654 is formed to permit an operator to cover the groove 654 with the operator's thumb, so that there is a sufficient seal between the tubular member 624 and the connector 610 to allow the operator to perform the flushing or drawing procedure on the tubular member 624. In the alternative, a partial cover sleeve 656 (only shown in FIG. 11) may be rotatably mounted over the entire connector 610. The cover sleeve 656 is rotated over the longitudinal groove 654 to provide a sufficient seal to enable the operator to perform the flushing or drawing procedure.

It is apparent to one skilled in the art that the connector can take on a number of other shapes than those described in FIGS. 1–11 so that the connector can be more easily incorporated to form a temporary seal with a number of different shaped medical devices. For example, other alternative embodiments would be a connector wherein the flushing lumen within the distal portion of the connector increases in size nonlinearly to an intermediate diameter and then increases linearly in size from the intermediate diameter or vice versa.

It is relatively important that the distal portion of the connector be comprised from a material that will provide the proper characteristics so that the connector 10 and/or the tubular member 24 deform slightly under pressure to form a temporary seal 34. Preferably, the material forming the distal portion of the connector nearly matches the material forming the tubular member 24. Accordingly, for most tubular members, the connector will be formed out of a low density polyethylene. A copolymer such as SURLYN ™ manufactured by the Du Pont Company has proven to be a suitable material for the connector.

Although the present invention has been described with reference to preferred embodiments, workers skilled in the art will recognize that changes may be made in form and detail without departing from the spirit and scope of the invention. In particular, one skilled in the art will recognize that the connector can be adapted so that it can be attached to a variety of devices that could provide a means for forcing a fluid into the connector and through the inner lumen of a catheter and/or drawing a foreign material from the inner lumen and into the connector.

What is claimed is:

1. An apparatus for flushing or drawing foreign material from an inner lumen of a tubular member, the apparatus comprising:
   a connector having a proximal end and a distal end with a flushing lumen extending therethrough, the connector having a distal portion wherein the flushing lumen increases in size from a first proximal cross-sectional area to a second larger distal cross-sectional area so that an annular surface within the distal portion will press against an end of the tubular member when the end of the tubular member is inserted into the distal portion, thereby creating a temporary fluid seal between the connector and the tubular member.

2. The apparatus of claim 1 wherein the distal portion of the flushing lumen has a flange, the flange being of a size so that at least a portion of the flange extends into the inner lumen when the tubular member is pressed against the annular surface.

3. The apparatus of claim 2 wherein the annular surface which presses against the end of the tubular member is on the flange.

4. The apparatus of claim 1 wherein the connector has a fitting on its proximal end for attaching a flushing fluid source to the connector.

5. The apparatus of claim 4 wherein the fitting is a luer fitting.

6. The apparatus of claim 5 wherein the flushing fluid source is a syringe containing flushing fluid.

7. The apparatus of claim 1 wherein the connector has a fitting for attaching a suction source to the connector.

8. The apparatus of claim 7 wherein the fitting is a luer fitting.

9. The apparatus of claim 8 wherein the suction source is a syringe.

10. The apparatus of claim 1 wherein the flushing lumen within the distal portion of the connector linearly increases in size from a first proximal diameter to a second larger distal diameter.

11. The apparatus of claim 1 wherein the flushing lumen within the distal portion of the connector nonlinearly increases in size from a first proximal diameter to a second larger distal diameter.

12. The apparatus of claim 1 wherein the flushing lumen within the distal portion of the connector linearly increases in size from a first proximal diameter to an intermediate diameter, remains constant at the intermediate size to create an intermediate step within the flushing lumen, and then linearly increases in size to a second larger distal diameter.

13. The apparatus of claim 1 wherein the flushing lumen within the distal portion of the connector nonlinearly increases in size from a first proximal diameter to an intermediate diameter, remains constant at the intermediate diameter to create an intermediate step within the flushing lumen, and then nonlinearly increases in size to a second larger distal diameter.

14. The apparatus of claim 1 wherein the inner lumen of the tubular member is a guide wire lumen of a catheter.

15. The apparatus of claim 1 wherein the tubular member is part of a tissue collecting device.

16. The apparatus of claim 2 wherein the flushing lumen extends through the flange so that the flushing lumen will be in coaxial alignment with the inner lumen of the tubular member when the end of the tubular member is inserted into the distal portion.

17. A method for flushing an inner lumen of a tubular member, the method comprising the steps of:
   providing a connector having a proximal end and a distal end with a flushing lumen extending therethrough, the connector having a fitting on its proximal end and having a distal portion wherein the flushing lumen increases in size from a first proximal cross-sectional area to a second larger distal cross-sectional area so that an annular surface within the distal portion will press against an end of the tubular member when the end of the tubular member is inserted into the distal portion;
   attaching a source of flushing fluid to the fitting;
   guiding a first end of the tubular member into the flushing lumen of the distal portion of the connector;

pressing the first end of the tubular member against the annular surface, to create a temporary fluid-tight seal between the tubular member and the connector; and forcing fluid from the source of flushing fluid through the connector and into the first end of the tubular member to flush fluid and foreign material from the inner lumen and out of a second end of the tubular member.

18. A method for drawing fluid through an inner lumen of a tubular member, the method comprising the steps of:

providing a connector having a proximal end and a distal end with a flushing lumen extending therethrough, the connector having a fitting on its proximal end and having a distal portion wherein the flushing lumen increases in size from a first proximal cross-sectional area to a second larger distal cross-sectional area so that an annular surface within the distal portion will press against an end of the tubular member when the end of the tubular member is inserted into the distal portion;

attaching a suction source to the fitting;

providing a flushing fluid source containing a flushing fluid;

guiding a first end of the tubular member into the flushing lumen of the distal portion of the connector;

pressing the first end of the tubular member against the annular surface, to create a temporary fluid-tight seal between the tubular member and the connector;

guiding the tubular member within the flushing fluid source so that the inner lumen is in fluid communication with the flushing fluid; and drawing fluid from the source of flushing fluid through the inner lumen and into the connector.

19. A method for drawing foreign materials from an inner lumen of a tubular member, the method comprising the steps of:

providing a connector having a proximal end and a distal end with a flushing lumen extending therethrough, the connector having a distal portion wherein the flushing lumen increases in size from a first proximal cross-sectional area to a second larger distal cross-sectional area so that an annular surface within the distal portion of will press against an end of the tubular member when the end of the tubular member is inserted into the distal portion;

guiding a first end of the tubular member into the flushing lumen of the distal portion of the connector;

pressing a first end of the tubular member against the annular surface, to create a temporary fluid-tight seal between the tubular member and the connector;

drawing the foreign materials from the inner lumen and into the connector.

20. An apparatus for flushing or drawing foreign material from an inner lumen of a tubular member, the apparatus comprising:

a connector having a proximal end and a distal end with a flushing lumen extending therethrough, the connector having a distal portion for receiving the tubular member and a flange protruding within the distal portion, the flange being of a size so that at least a portion of the flange extends into the inner lumen when the tubular member is inserted into the distal portion, wherein the flushing lumen extends through the flange so as to be in coaxial alignment with the inner lumen when the end of the tubular member is inserted into the distal portion.

21. The apparatus of claim 20 wherein the flushing lumen increases in size from a first proximal cross-sectional area to a second larger distal cross-sectional area so that an annular surface within the distal portion will press against the end of the tubular member when the end of the tubular member is inserted into the distal portion.

22. The apparatus of claim 20 wherein tubular member has an outer diameter and wherein the flushing lumen at the distal end of the connector has a cross-sectional area substantially greater than the outer diameter of the tubular member for facilitating insertion of the tubular member into the distal portion.

23. An apparatus for flushing or drawing foreign material from an inner lumen of a tubular member having an outer diameter, the apparatus comprising:

a connector having a proximal end and a distal end with a flushing lumen extending therethrough, the connector having a distal portion having a distal cross-sectional area at the distal end which is substantially larger than the outer diameter of the tubular member to facilitate insertion of the end of the tubular member into the distal end of the connector; and means for sealing between the connector and the tubular member.

24. The apparatus of claim 23 wherein the mans for sealing comprises an annular surface within the distal portion of the connector, wherein the annular surface presses against an end of the tubular member when the end of the tubular member is inserted into the distal portion, thereby creating a temporary fluid seal between the connector and the tubular member.

* * * * *

UNITED STATES PATENT AND TRADEMARK OFFICE
CERTIFICATE OF CORRECTION

PATENT NO. : 5,320,613

DATED : June 14, 1994

INVENTOR(S) : REED A. HOUGE, THOMAS V. RESSEMANN, LOUIS G. ELLIS

It is certified that error appears in the above-indentified patent and that said Letters Patent is hereby corrected as shown below:

Col. 5, line 47, delete "diagramed", insert --diagrammed--

Col. 6, line 25, delete "surface 42", insert --surface 421--

Col. 7, line 37, delete "SURLYN TM", --insert --SURLYN™--

Col. 10, line 47, delete "mans", insert --means

Signed and Sealed this

First Day of November, 1994

Attest:

BRUCE LEHMAN

Attesting Officer      *Commissioner of Patents and Trademarks*